United States Patent [19]

Nakashima et al.

[11] Patent Number: 6,028,094
[45] Date of Patent: Feb. 22, 2000

[54] AGENT FOR PREVENTION AND SUPPRESSION OF DRY COUGHING CAUSED BY ANGIOTENSIN CONVERTING ENZYME INHIBITORS

[75] Inventors: Mitsuyoshi Nakashima; Kazuo Umemura, both of Shizuoka, Japan

[73] Assignees: Kissei Pharmaceutical Co., Ltd., Nagano; Ono Pharmaceutical Co., Ltd., Osaka, both of Japan

[21] Appl. No.: 09/077,805

[22] PCT Filed: Dec. 13, 1996

[86] PCT No.: PCT/JP96/03643

§ 371 Date: Jun. 15, 1998

§ 102(e) Date: Jun. 15, 1998

[87] PCT Pub. No.: WO97/22362

PCT Pub. Date: Jun. 26, 1997

[30] Foreign Application Priority Data

Dec. 15, 1995 [JP] Japan .................................... 7-351734

[51] Int. Cl.[7] ..................................................... A01N 43/50
[52] U.S. Cl. ............................................ 514/399; 514/396
[58] Field of Search ...................................... 514/399, 396

[56] References Cited

PUBLICATIONS

Umemura, K. et al., Altered prostaglandin metabolism induced by angiotensin converting enzyme inhibitors in broncho–alveolar lavage fluid of ginea pig. Jpn. J. Pharmacology. 1996, vol. 72, No. 1, pp. 17–21.

Puolijoki, H. et al., cough induced by enalapril byt not by captopril. European Respiratory Journal. Mar. 1989 vol. 2, No. 3, pp. 289–291.

Naomi et al., "Role of endogenous Thromboxane A2 on Dry Cough Induced by Angiotensin Converting Enzyme Inhibitor", Abstract to Therapeutic Research, vol. 14, No. 7, 1993.

Naito et al., "Effects of thromboxane synthetase inhibitors on aggregation of rabbit platelets", Abstract to Eur. J. Pharmacol. 91(1), pp. 41–48, 1983.

*Primary Examiner*—Dwayne C. Jones
*Attorney, Agent, or Firm*—Sughrue, Mion, Zinn, Macpeak & Seas , PLLC

[57] ABSTRACT

The present invention is to provide an agent for the prevention and depression of dry coughing caused by angiotensin converting enzyme inhibitors which comprises a thromboxane synthetase inhibitor or thromboxane receptor antagonist as the active ingredient. Administering the drug is effective in preventing and depressing dry coughing caused by angiotensin converting enzyme inhibitors. For example, the use of the drug in combination with ozagrel hydrochloride was found to be effective in significantly dry coughing in hypertonic patients suffering from dry coughing attributable to the administration of captopril.

2 Claims, 1 Drawing Sheet

AGENT FOR PREVENTION AND SUPPRESSION OF DRY COUGHING CAUSED BY ANGIOTENSIN CONVERTING ENZYME INHIBITORS

This application is a 371 of PCT/JP96/03643, filed on Dec.13, 1996.

TECHNICAL FIELD

The present invention relates to an agent for the prevention and depression of dry coughing caused by angiotensin converting enzyme inhibitors, characterized in comprising a thromboxane synthetase inhibitor or thromboxane receptor antagonist as the active ingredient.

BACKGROUND ART

Angiotensin converting enzyme inhibitors are effective antihypertensive drugs and also have preventive effects on the development into cardiac insufficiency and hypertrophy of the heart in hypertensive disease. Therefore, these drugs have been extensively used in the world as one of the first choice drugs for the treatment of hypertension and are very highly useful medicaments.

However, the angiotensin converting enzyme inhibitors, for example, captopril and enalapril have been reported to cause dry coughing as one of their side effects with an incidence of 15–20% and 10–33%, respectively (Arch. Intern. Med., Vol. 145, p. 1524 (1985); Arch. Intern. Med., Vol. 148, p. 249(1988); American Heart Journal, Vol. 116, p. 1658(1988); N. Z. Med. J., Vol. 100, pp. 161–163 (1987); British Medical Journal, Vol. 294, pp. 1521–1523 (1987); British Medical Journal, Vol. 299, pp. 12–16 (1989)). Thus, the use of these drugs become impossible in many patients from the above reason, and the treatment for hypertension in such patients is not sufficient.

Accordingly, in the use of highly useful angiotensin converting enzyme inhibitors, it has been greatly desired to develop drugs which depress dry coughing as the side-effect, preferably, without attenuation of their antihypertensive effects.

For resolving this problem, many studies to alleviate the dry coughing have been carried out. However, the mechanism of dry coughing induced by angiotensin converting enzyme inhibitors has not been clearly elucidated yet.

Up to date, it has been advocated as one of the mechanism of the dry coughing induction that bradykinin which accumulates in the process of the conversion of angiotensin I into angiotensin II by angiotensin converting enzyme causes the release of tachykinins (substance P, neurokinin A), and then, the tachykinins stimulate the c-fibers whose activation causes coughing (British Medical Journal, Vol. 294, pp. 1521–1523 (1987); British Medical Journal, Vol. 299, pp. 12–16 (1989); J. Appl. Physiol., Vol. 48, pp. 511–517 (1980); Nature, Vol. 264, pp. 451–453 (1976)).

On the other hand, it has been reported that sulindac, indomethacin and sodium cromoglycate (Intal®) depressed the dry coughing (THE LANCET, p. 872 (1987); Journal of Cardiovascular Pharmacology, Vol. 19, No. 15, pp. 670–673 (1992); THE LANCET, Vol. 345, pp. 13–16 (1995)). It is also known that indomethacin attenuated the antihypertensive effects of angiotensin converting enzyme inhibitors in patients with essential hypertension (Journal of Hypertension, Vol. 5, pp. 121–128 (1987)). Furthermore, the use of conventional antitussive remedy was not effective in dry coughing caused by angiotensin converting enzyme inhibitors.

Although studies to develop drugs effective in depressing dry coughing caused by angiotensin converting enzyme inhibitors are being eagerly promoted, such drugs which can be put to practical use have not been found.

DISCLOSURE OF INVENTION

The present invention relates to an agent for the prevention and depression of dry coughing caused by angiotensin converting enzyme inhibitors, characterized in comprising a thromboxane synthetase inhibitor or thromboxane receptor antagonist as the active ingredient.

BEST MODE FOR CARRYING OUT THE INVENTION

Figure 1:
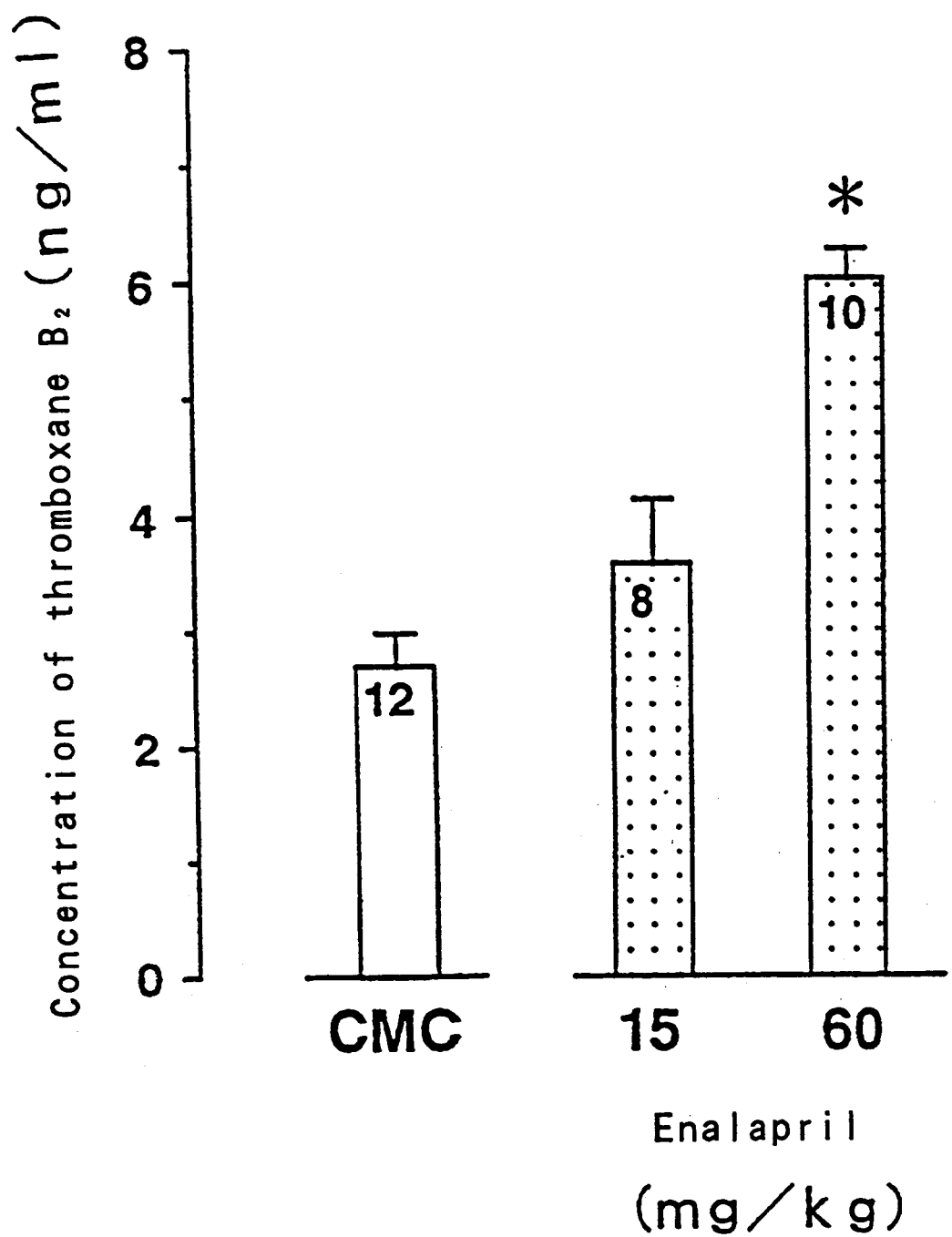
FIG. 1 is a graph illustrating the result of influence of enalapril on thromboxane $B_2$ concentration in guinea-pig broncho-alveolar lavage fluid. The axis of ordinates shows thromboxane $B_2$ concentration. The axis of abscissas shows kind and dose of administered drugs. The data show means and standard deviation. The number in columns shows the number of animals. The group marked with * shows the significantly different from the CMC-treated group at $p<0.05$.

We, the present inventors, have been eagerly studied on dry coughing caused by angiotensin converting enzyme inhibitors. As a result, we confirmed that there is a close correlation between thromboxane $A_2$ and the incidence of dry coughing and also found that thromboxane synthetase inhibitors, which inhibit thromboxane $A_2$ synthesis, or thromboxane receptor antagonists, which prevent the actions of thromboxane $A_2$, have excellent depressive effects on the above dry coughing without affecting the antihypertensive effects of angiotensin converting enzyme inhibitors. Thereby, the present invention has been resulted in the accomplishment.

In in vivo experiment using guinea-pigs, it was confirmed that the content of thromboxane $B_2$, a metabolite of thromboxane $A_2$, in broncho-alveolar lavage fluid after the administration of enalapril, one of angiotensin converting enzyme inhibitors, was significantly increased, compared with the control group to which no enalapril was administered. This result suggests that thromboxane $A_2$ is rapidly produced by administering angiotensin converting enzyme inhibitors, and that there is a close correlation between the administration of angiotensin angiotensin converting enzyme inhibitors and the production of thromboxane $A_2$.

From the above finding, we thought that the drugs which inhibit thromboxane $A_2$ synthesis or to prevent the actions of thromboxane $A_2$ are able to use for the prevention or depression of dry coughing caused by angiotensin converting enzyme inhibitors. To confirm this matter, an angiotensin converting enzyme inhibitor in combination with a thromboxane synthetase inhibitor was given to the patients with hypertension who had developed dry coughing attributable to angiotensin converting enzyme inhibitors at several days after administrating the angiotensin converting enzyme inhibitor. As a result, remarkable change in frequency and degree of dry coughing was observed without affecting the antihypertensive effect of the angiotensin converting enzyme inhibitor, and therefore symptoms of the dry coughing was improved.

In conclusion, thromboxane $A_2$ relates to dry coughing caused by angiotensin converting enzyme inhibitors.

Therefore, thromboxane synthetase inhibitors, which inhibit thromboxane $A_2$ synthesis, or thromboxane receptor antagonists, which prevent the actions of thromboxane $A_2$, are useful drugs having preventive and depressive effects on the dry coughing induced after taking angiotensin converting enzyme inhibitors. These drugs also have effects on release from the irregularly and occasionally severe dry coughing, on ensuring enough sleep which is prevented by the dry coughing, and on so on. Accordingly, also in the hypertonic patients to whose angiotensin converting enzyme inhibitors are unable to be used owing to dry coughing, the present invention makes it possible to use angiotensin converting enzyme inhibitors and to do sufficient treatment.

In the present invention, a drug that has inhibitory activity on thromboxane synthetase can be used as a thromboxane synthetase inhibitor. As examples of such thromboxane synthetase inhibitors, ozagrel hydrochloride (chemical name: 4-(1H-imidazol-1-ylmethyl)cinnamic acid hydrochloride), imitrodast (chemical name: sodium 2-[(1H)-1-imidazolylmethyl]-4,5-dihydrobenzo[b] thiophene-6-carboxylate), isbogrel (chemical name: 7-phenyl-7-(3-pyridyl)-6-heptenoic acid), E-3040 (chemical name: 5,7-dimethyl-2-(methylamino)-4-(3-pyridylmethyl)-6-benzotiazolol), E-6700 (chemical name: (E) 2-[(4-methoxy-2,5-dimethyl-3,6-dioxo-1,4-cyclohexadien-1yl) methylene]-7-(3-pyridyl) heptanoic acid), KDI-792 (chemical name: (+)-(5Z)-6-[(2S, 4R)-4-(4-chlorophenylsulfonylamino)-1-(3-pyridylmethyl)-2-pyrrolidinyl]-5-hexenoic acid hydrochloride), Y-20811(chemical name: sodium 4-[α-hydroxy [5-(1H-imidazol-1-yl)-2-methylphenyl]methyl]-3, 5-dimethylbenzoate), NM-702 (chemical name: 4-bromo-5-(3-pyridylmethylamino)-6-[3-(4-chlorophenyl) propoxy ]-3 (2H)pyridazinone), KY-234 (chemical name: 1-[3-(4-diphenylmethyl-1-piperazinyl)propyl]-3-(1H-imidazol-1ylmethyl)-1H-indole-6-carboxylic acid), TER-930180 (chemical name; 4-[1-(chlorophenylsulfonylaminomethyl)-4-(3-pyridyl)butyl]phenylpropionic acid), nafagrel hydrochloride (chemical name: 2-(1H-imidazol-1-ylmethyl)-1,2, 3,4-tetrahydronaphthalene-6-carboxylic acid hydrochloride), pharmaceutically acceptable salts thereof or free compounds thereof can be illustrated.

In the present invention, a drug that competes with thromboxane and prevents action to thromboxane receptor can be used as a thromboxane receptor antagonist. As examples of such thromboxane receptor antagonists, seratrodast (chemical name: 7-phenyl-7-(2,4,5-trimethyl-3,6-dioxo-1,4-cyclohexadien-1yl) heptanoic acid), S-1452 (chemical name: calcium salt of (Z)-[1R-[1 α, 2 α, 3 β, 4 α]]-7-[3-(phenylsulfonylamino)bicyclo [2.2.1]hept-2-yl)-5-heptenoic acid), vapiprost (chemical name: (Z)-[1R-[1 α, 2 β, 3 β, 5 α]]-7-[5-([1,1'-biphenyl]-4-ylmethoxy)-3-hydroxy-2-(1-piperidinyl)-cyclopentyl]-4-heptenoic acid), Bay-u-3405 (chemical name: 3-[(3R)-(4-fluorophenylsulfonylamino)-1,2,3,4-tetrahydro-9H-carbazol-9-yl]propionic acid), KDI-792 (chemical name; (+)-(5Z)-6-[(2S, 4R)-4-(4-chlorophenylsulfonylamino)-1-(3-pyridylmethyl)-2-pyrrolidinyl]-5-hexenoic acid hydrochloride), KT2-962 (chemical name: sodium 3-[4-(4-chlorophenylsulfonylamino)butyl]-6-(1-methylethyl)-1-azulenesulfonate), F-1322 (chemical name: N-[2-[4-(diphenylmethoxy)-1-piperidinyl]ethyl]--3-hydroxy-5-(3-pyridylmethoxy)-2-naphthalene carboxamide), Z-335 (chemical name: sodium [2-(4-chlorophenylsulfonylaminomethyl)-2,3-dihydro-1H-inden-5-yl]acetate), KW-3635 (chemical name: sodium 11-[2-(5, 6-dimethyl-1H-benzimidazol-1-yl) ethylidene]-6,11-dihydrobenzo[b, e]oxepin-2-carboxylate), pharmaceutically acceptable salts thereof or free compounds thereof can be illustrated.

In the present invention, as examples of angiotensin converting enzyme inhibitors, captopril, enalapril, lisinopril, delapril, alacepril, cilazapril, benazepril, temocapril and the like, pharmaceutical acceptable salts thereof or free compounds thereof can be illustrated.

The pharmaceutically acceptable salts of the present invention refer to common salts. Examples of such salts include acid addition salts with mineral acids such as hydrochloric acid, hydrobromic acid, hydroiodic acid, sulfuric acid, nitric acid and phosphoric acid, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid and aspartic acid, salts with organic amines such as lysine, and salts with inorganic bases such as a sodium salt, a potassium salt and a calcium salt.

In addition, the pharmaceutically acceptable salts of the present invention also include hydrates thereof and solvates thereof with pharmaceutically acceptable solvents such as ethanol.

The above known compounds illustrated as thromboxane synthetase inhibitors or thromboxane receptor antagonists used in the present invention can be prepared by known methods described in literatures or modified methods thereof. In case of thromboxane synthetase inhibitors or thromboxane receptor antagonists having an asymmetric carbon atom, two isomers of (R) configuration and (S) configuration in each asymmetric carbon atom exist. Either one of the isomers and a mixture thereof can be used in the present invention. In the compounds having an unsaturated bond, two geometrical isomers exist. Either one of cis (Z) isomer or trans (E) isomer can be used in the present invention.

Thromboxane synthetase inhibitors or thromboxane receptor antagonists of the present invention are administered orally or parenterally in the form of appropriate pharmaceutical compositions such as tablets, powders, fine granules, granules, capsules, injections and the like. These pharmaceutical compositions can be formulated in accordance with conventional methods using conventional pharmaceutical carriers, excipients and other additives.

Of the above pharmaceutical compositions, in formulating tablets, powders, fine granules, granules, capsules and the like, conventional excipients, disintegrators, binders, lubricants and the like can be used. Sugars or sugar alcohols such as D-mannitol, lactose and sucrose, starches or starch derivatives such as wheat starch, rice starch, corn starch, potato starch, pregelatinized starch, partly pregelatinized starch, dextrin, cyclodextrin, pullulan and hydroxypropylstarch, celluloses or cellulose derivatives such as crystalline cellulose, crystalline cellulose.carmellose sodium, methylcellulose and hydroxypropylmethylcellulose, sodium alginate, acacia, agar, macrogol, aluminium stearate, aluminium monostearate and the like can be used as excipients, and calcium hydrogenphosphate, anhydrous calcium hydrogenphosphate, magnesium aluminometasilicate, synthetic aluminum silicate, synthetic hydrotalcite, aluminum hydroxide, magnesium hydroxide, calcium phosphate, dried aluminum hydroxide gel, precipitated calcium carbonate, light anhydrous silicic acid and the like can be used as mineral excipients. The application of these materials is not limited to excipients, and these materials can be used as disintegrators or binders.

Carmellose calcium, carmellose, low substituted hydroxypropylcellulose, sodium carboxymethylstarch, croscarmellose sodium, tragacanth, starches or starch derivatives such as wheat starch, rice starch, cornstarch, potato starch, pregelatinized starch, partly pregelatinized starch, dextrin, pullulan and hydroxypropylstarch, and the like can be used as disintegrators. The application of these materials is not limited to disintegrators, and these materials can be used as excipients.

Hydroxyethylcellulose, hydroxypropylcellulose, polyvinyl alcohol, polyvinylpyrrolidone, starches or starch derivatives such as wheat starch, rice starch, corn starch, potato starch, pregelatinized starch, partly pregelatinized starch, dextrin, pullulan and hydroxypropylstarch, and the like can be used as binders.

Calcium stearate, magnesium stearate, stearic acid, talc, cetanol, polyoxy 40 stearate, leucine, hydrogenated oil, sodium lauryl sulfate, paraffin, polyoxyethyleneglycol fatty acid ester, fatty acid ester and the like can be used as lubricants. The application of these materials is not limited to lubricants, and these materials can be used as excipients.

In formulating tablets, tablets can be coated with film using lactose, saccharose, gelatin, hydroxypropylcellulose, hydroxypropylmethylcellulose, polyvinylacetal diethylaminoacetate, metaacrylic acid copolymer, hydroxypropylmethylcellulose phthalate or the like.

In formulating injections, distilled water, isotonic sodium chloride solution, alcohol, glycerin, poly alcohol, vegetable oil and the like can be used as diluents. These preparations may further contain buffers, isotonicities, antiseptics, moistening agents, emulsifiers, dispersing agents, stabilizing agents, dissolving aids and the like.

The dosage is appropriately decided depending on the kind of used thromboxane synthetase inhibitor or thromboxane receptor antagonist, the sex, age, body weight, degree of symptoms and the like of each patient to be treated, which is approximately within the range of from 1 to 1,000 mg per day per adult human in the case of oral administration and approximately within the range of from 0.1 to 100 mg per day per adult human in the case of parenteral administration, and the daily dose is divided into one to several doses per day.

EXAMPLE

The present invention is further illustrated in more detail by way of the following Examples. The present invention is not limited thereto, and thromboxane synthetase inhibitors, thromboxane receptor antagonists and angiotensin converting enzyme inhibitors are not limited to those described above.

Test Example 1
Influence on the Thromboxane $B_2$ Synthesis in Bronchoalveolar Lavage Fluid of Guinea-pigs Male Hartley guinea-pigs weighting 250–300 g were used. Enalapril (15 or 60 mg/kg) was dissolved into 0.5% carboxymethylcellulose (CMC) and was orally administered once a day for 2 weeks. In the control group, CMC was administered as same schedule.

Twenty-four hours after the final administration, for the broncho-alveolar lavage fluid sampling, the guinea pigs were inserted the cannula into the trachea under anesthesia with penotbarbital. Then, the lung was 5 times washed with 5 ml of 37° C. saline, and 3–4 ml of broncho-alveolar lavage fluid sample was collected. Thirty $\mu$M of indomethacin was applied into the broncho-alveolar lavage fluid, and then, it was centrifuged at 3000 rpm for 10 minutes at 4° C. The supernatant was freezed at −80° C. until the measurement. Thromboxane $B_2$ which is the metabolite of thromboxane $A_2$ was measured by enzyme immunoassay.

As shown in FIG. 1, the concentration of thromboxane $B_2$ which is the metabolite of thromboxane $A_2$ in bronchoalveolar lavage fluid after the administration of enalapril for 2 weeks increased dose-dependently, especially it was significant at the dose of 60 mg/kg. This result shows that the administration of angiotensin converting enzyme inhibitor remarkably induces the thromboxane $A_2$ synthesis.

Test Example 2
Therapeutic Effect of Thromboxane Synthetase Inhibitor on the Dry Coughing Caused by Angiotensin Converting Enzyme Inhibitor Two patients (a man aged 73 years and a woman aged 80 years) with hypertension who developed dry coughing during antihypertensive therapy with captopril (37.5 mg/day) were studied. Ozagrel (200 mg) was continually co-administered twice a day with captopril, and the coughing severity were observed on the 14th day after the start of the ozagrel treatment.

As a result, by the co-treatment with ozagrel and captopril, the remarkable inhibition of coughing induction without influence on the antihypertensive effect was confirmed. In the man who had suffered from severe coughing developed, especially at night, after the several days of captopril treatment, the coughing was almost disappeared, and the patient was released from the coughing at night. The dry coughing in this patient was improved significantly. In the woman who had suffered from moderate coughing developed both at day and night after the several days of captopril treatment, the intensity and frequency of coughing were remarkably decreased. The dry coughing in this patient was improved moderately

INDUSTRIAL APPLICABILITY

Agents of the present invention comprising a thromboxane synthetase inhibitor or thromboxane receptor antagonist as the active ingredient have activities on the depression of dry coughing induced by taking an angiotensin converting enzyme inhibitor and therefore are effective as agents for the prevention and depression of dry coughing induced by taking angiotensin converting enzyme inhibitors.

We claim:

1. An agent for the suppression of dry coughing caused by an angiotensin converting enzyme inhibitor (ACEI) wherein said agent is a thromboxane synthetase inhibitor and said inhibitor is ozagrel or a pharmaceutically acceptable salt thereof present in a therapeutically effective amount to suppress dry coughing.

2. A method for the suppression of dry coughing caused by an angiotensin converting enzyme inhibitor comprising administering a thromboxane synthetase inhibitor and said inhibitor is ozagrel or a pharmaceutically acceptable salt thereof, administered in a therapeutically effective amount to suppress dry coughing.

* * * * *